(12) United States Patent
Li et al.

(10) Patent No.: US 7,257,897 B2
(45) Date of Patent: Aug. 21, 2007

(54) TRIMMER FOR CUTTING A COILED STRAND

(75) Inventors: Zhigang Li, Hillsborough, NJ (US); Yufu Li, Bridgewater, NJ (US); Ronald W Marsh, Hackettstown, NJ (US); Kevor S. Tenhuisen, Clinton, NJ (US)

(73) Assignee: Ethicon, Inc., Somerville, NJ (US)

(*) Notice: Subject to any disclaimer, the term of this patent is extended or adjusted under 35 U.S.C. 154(b) by 681 days.

(21) Appl. No.: 10/302,535

(22) Filed: Nov. 22, 2002

(65) Prior Publication Data
US 2004/0102800 A1 May 27, 2004

(51) Int. Cl.
*B26B 13/00* (2006.01)
(52) U.S. Cl. ............... 30/258; 30/289; 83/907
(58) Field of Classification Search .......... 30/91.2, 30/134, 229, 258, 289, 232, 278, 279.2; 83/907; 606/167, 174
See application file for complete search history.

(56) References Cited

U.S. PATENT DOCUMENTS

| 251,604 A * | 12/1881 | Lane .................... 606/175 |
| 2,292,729 A * | 8/1942 | Woodward ............ 30/91.2 |
| 2,691,416 A * | 10/1954 | Williams et al. ........ 83/573 |
| 3,581,400 A | 6/1971 | Snead ..................... 433/4 |
| 5,046,252 A * | 9/1991 | Ayuta et al. ........... 30/258 |
| 5,101,563 A * | 4/1992 | d'Orgelys ............... 30/28 |
| 5,966,815 A | 10/1999 | Sheikh .................. 30/124 |
| 6,061,912 A | 5/2000 | Gazaway ............... 30/140 |
| 6,123,001 A | 9/2000 | Andrich ................. 83/13 |

FOREIGN PATENT DOCUMENTS

| GB | 855166 | 11/1960 |
| GB | 1000219 | 8/1965 |
| GB | 2013125 | 8/1979 |
| GB | 2350080 | 11/2000 |
| WO | 9639983 | 12/1996 |

* cited by examiner

*Primary Examiner*—Boyer D. Ashley
*Assistant Examiner*—Carolyn T Blake

(57) ABSTRACT

A cutting device for trimming a coiled strand, such as an arterial, urinary or other intraluminal stent made from metal or plastic wire, has a pair of articulating arms connected at a pivot joint. One of the arms has a holding jaw for holding the coiled strand. A second of the arms has a jaw with a cutter. The holding jaw has a passageway through which the coiled strand may be threaded to aid in holding the coiled strand for cutting by the cutter. The holding jaw preferably has a guide channel formed by a pair of tapered walls that slide between adjacent turns of the coiled strand. In accordance with a method of the invention, an end of the coiled strand is introduced through the passageway in the holding jaw. The coiled strand is rotated to advance the coiled strand through the passageway until the coiled strand is positioned beneath the cutting jaw at the selected location. The lever portions and the jaw portions are then urged together, cutting the coiled strand at the selected location.

6 Claims, 5 Drawing Sheets

TRIMMER FOR CUTTING A COILED STRAND

FIELD OF THE INVENTION

The present invention relates to a trimmer for cutting a coiled strand, such as a polymer fiber or a strand of wire. More particularly, the present invention relates to a trimmer for cutting a coiled strand to a desired length prior to implantation in the body of a living creature, e.g., when the coiled strand is used as an arterial or urinary stent.

BACKGROUND OF THE INVENTION

Conventional pincer or scissor-action wire cutters are suitable for cutting straight or gently curved wires but are not optimal for cutting coiled wires. When trimming a coiled strand with multiple individual coil turns having no gaps or gaps between adjacent individual coil turns that are smaller than the thickness of the cutter's jaws, the adjacent coil turns must be spread apart in order for the jaws to close and make the cut. If the coil turns are spread beyond their elastic limit, they will be deformed, thus damaging the coil structure.

A scissor, pincher or guillotine cut each result in a cut end which has sharp edges. It is preferable for the terminal ends of a wire or fiber which is coiled for use as a prosthetic implant to be rounded to avoid inadvertently cutting or piercing bodily tissues when placing the implant and during its use. For example, if a coiled stent has a sharp end, it could readily pierce the wall of an artery or other internal luminal structure into which it is inserted. Because the optimal dimensions of surgical prostheses are sometimes not known prior to the initial stages of surgical intervention (e.g., during visualization via radiography) either a large selection of prostheses must be kept on hand or the prosthesis must be dimensioned at the time of use. Coiled prostheses, such as stents may be trimmed to provide an optimal length. As noted, conventional cutters leave a sharp cut end and may distort a coil such as a stent. Subsequent rounding of a sharp cut end, e.g., by abrasion, represents added expense, personnel, time, complexity and apparatus to the surgical procedure and may damage the coiled structure.

It would therefore be advantageous to have a coil trimmer that minimizes the deformation of the coil from cutting and produces a cut end with a reduced tendency to cut or pierce the bodily tissues that are exposed to the cut end.

SUMMARY OF THE INVENTION

The limitations of prior art cutting devices are addressed by the present invention, which includes a cutting device for trimming a coiled strand and having a pair of articulating arms pivotally connected at a pivot joint. Each of the pair of articulating arms have a lever portion disposed proximal to the pivot joint and a jaw portion disposed distal to the pivot joint. The jaw portions are urged together when the lever portions are urged together. A first of the jaw portions is a holding jaw for holding the coiled strand. A second of the jaw portions is a cutting jaw for cutting the coiled strand. The holding jaw has a passageway therein through which the coiled strand may be threaded to aid in holding the coiled strand for cutting by the cutting jaw at a selected location.

In accordance with a method of the present invention, a cutting device is provided having the characteristics described in the preceding paragraph. An end of the coiled strand is introduced through the passageway in the holding jaw. The coiled strand is rotated to advance the coiled strand through the passageway until the coiled strand is positioned beneath the cutting jaw at the selected location. The lever portions and the jaw portions are urged together cutting the coiled strand at the selected location.

DETAILED DESCRIPTION OF THE INVENTION

Figure 1:
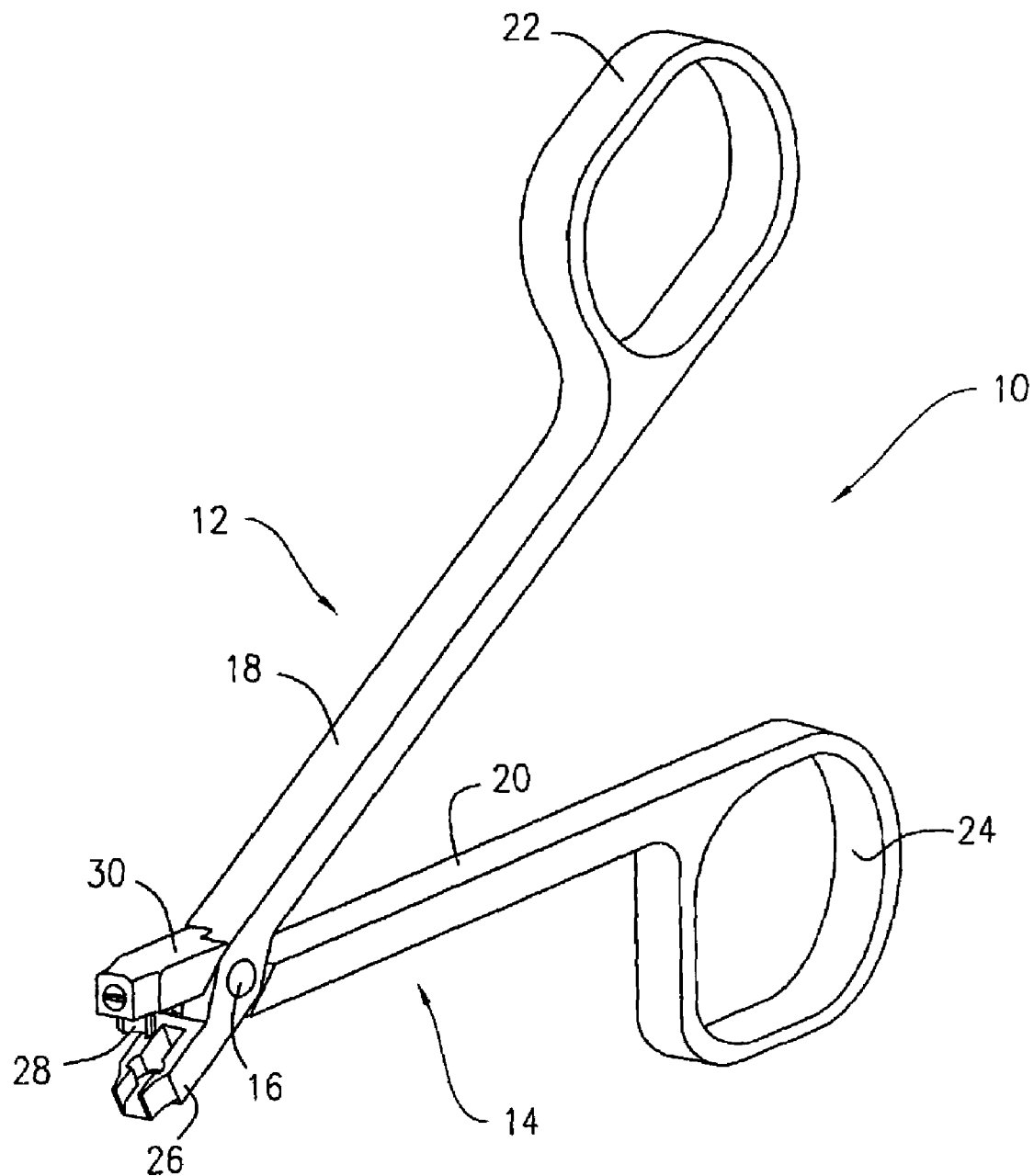
FIG. 1 is a perspective view of a trimmer constructed in accordance with an exemplary embodiment of the present invention.

FIG. 1 shows a trimmer 10 having a pair of opposed articulating arms 12, 14 pivotally connected in scissor fashion at the point of their crossing intersection by a pivot pin 16. Each arm 12, 14 has a lever portion 18, 20, respectively, with finger/thumb grips 22, 24 at a proximal end thereof. Arm 12 has a holding jaw 26 at the distal end thereof, beyond the pivot pin 16. As shall be explained more fully below, the holding jaw 26 holds a coiled strand such as a stent, for cutting by a cutter 28 extending from cutting jaw 30 disposed at the distal end of arm 14.

Figure 2:
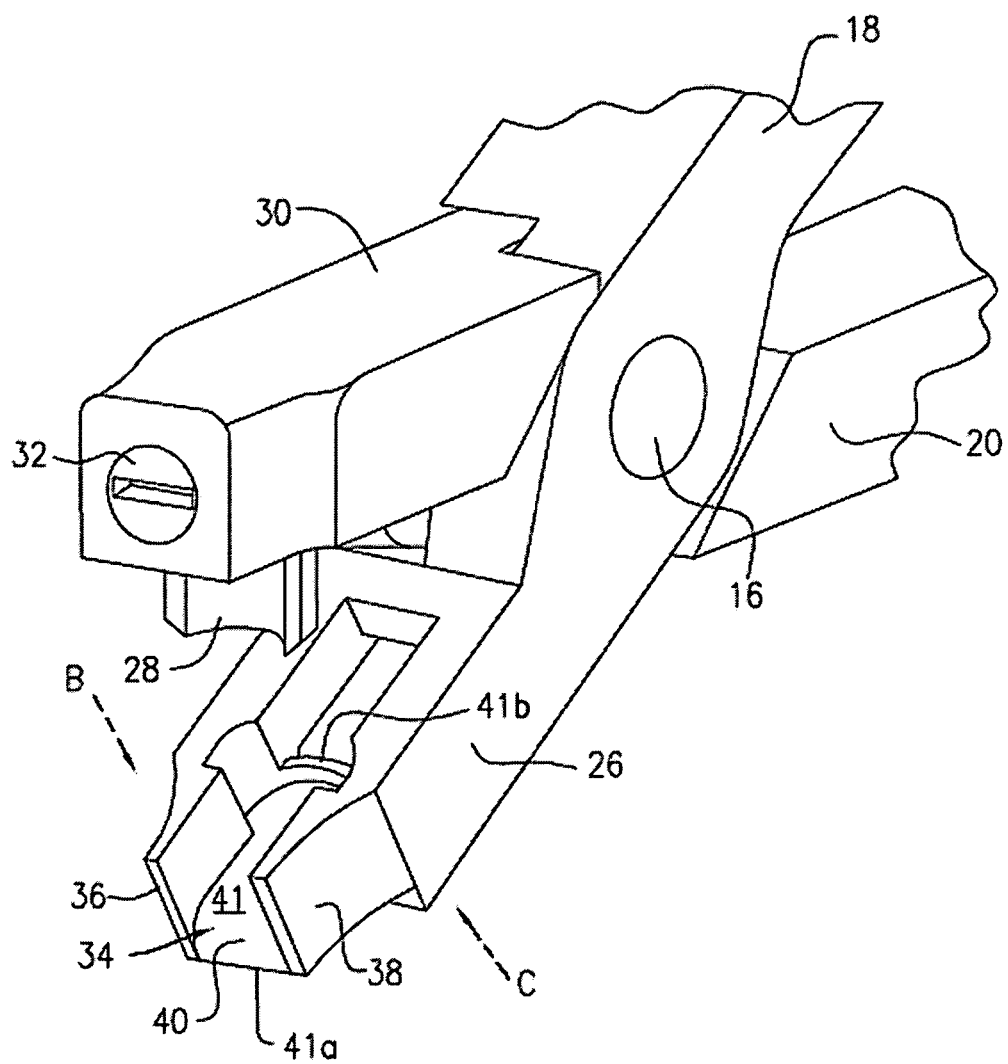
FIG. 2 is an enlarged view of holding and cutting jaws of the trimmer shown in FIG. 1.

FIG. 2 shows that the cutter 28 has an arcuate (semi-circular) cross-sectional shape and is removably retained within the cutting jaw 30 by retention screw 32. Alternatively, cutter 28 could be removably held in cutting jaw 30 by a taper, dovetail, snap, or could be permanently affixed, e.g., by gluing, welding, embedding or by monolithic formation which would be especially appropriate for a disposable trimmer 10.

Holding jaw 26 has a guiding channel 34 formed by two side walls 36, 38 and a bottom wall 40 with an upper surface 41. The upper surface 41 is radiused at the distal edge 41a thereof and at the proximal edge 41b. The side walls 36, 38 preferably have a taper such that they are thinner at the distal end thereof to aid in the insertion of the side walls 36, 38 between adjacent coil loops as described below in reference to FIG. 6.

Figure 3:
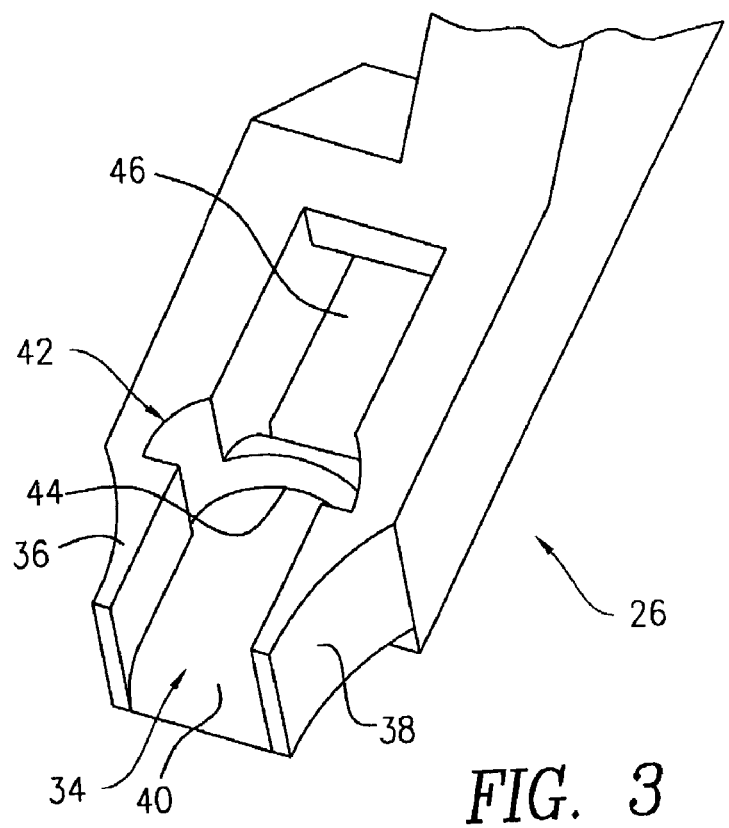
FIG. 3 is an enlarged view of a holding jaw of the trimmer of FIG. 2 viewed from the perspective indicated by the arrow emanating from the letter "B" in FIG. 2.

FIG. 3 shows that the holding jaw 26 has a cutter slot 42 having a cross-sectional shape that approximates that of the cutter 28. The cutter slot 42 is preferably provided with a sharp edge 44 which acts in opposition to the cutting edge 29 (see FIG. 2) of cutter 28 to shear the coil to be cut. A coil passageway 46 extends through the holding jaw 26. A coil to be cut may be threaded through coil passageway 46 as shall be described below.

Figure 4:
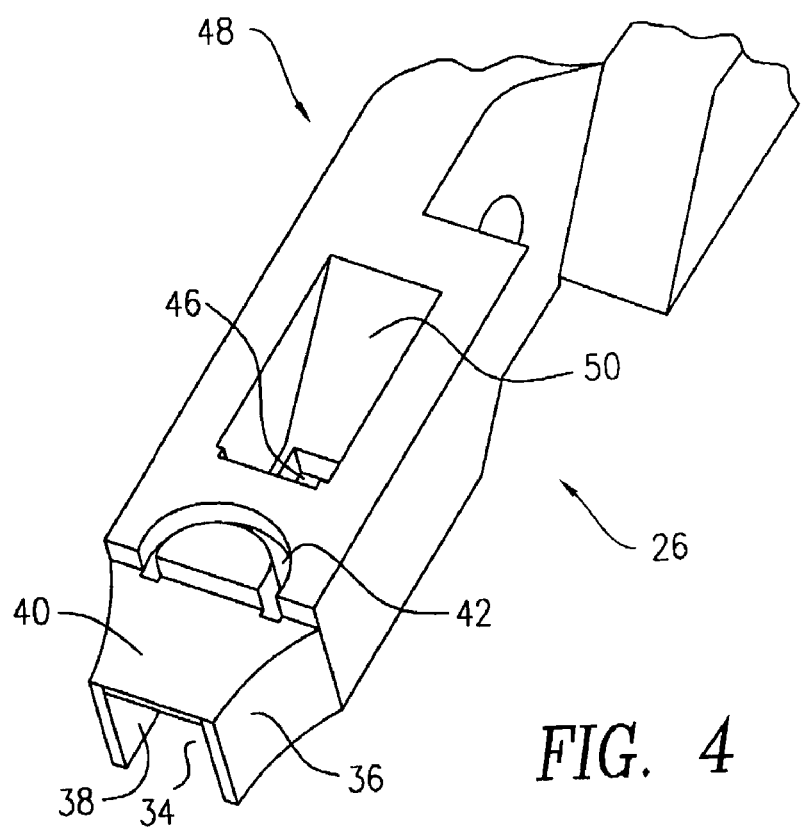
FIG. 4 is an enlarged view of the holding jaw of FIGS. 2 and 3 viewed from the perspective indicated by the arrow emanating from the letter "C" in FIG. 2.

FIG. 4 shows the bottom surface 48 of the holding jaw 26. In the embodiment shown, the cutter slot 42 extends through the bottom surface 48, as does the coil passageway 46, which flares outwardly along surface 50. While the guiding channel 34 shown is approximately a trough shape, it may have different cross-sectional shapes and sizes depending on the profile of the fiber or wire to be cut. The length of guiding channel 34 should be less than the inner diameter of the coiled fiber in order to prevent distortion of coils during loading onto the holding jaw 26 and cutting. Angled surface 50 has an angle relative to surface 48 ranging from 30° to 60° for guiding the coiled strand (see 58 in FIG. 6) through passageway 46.

Figure 5:
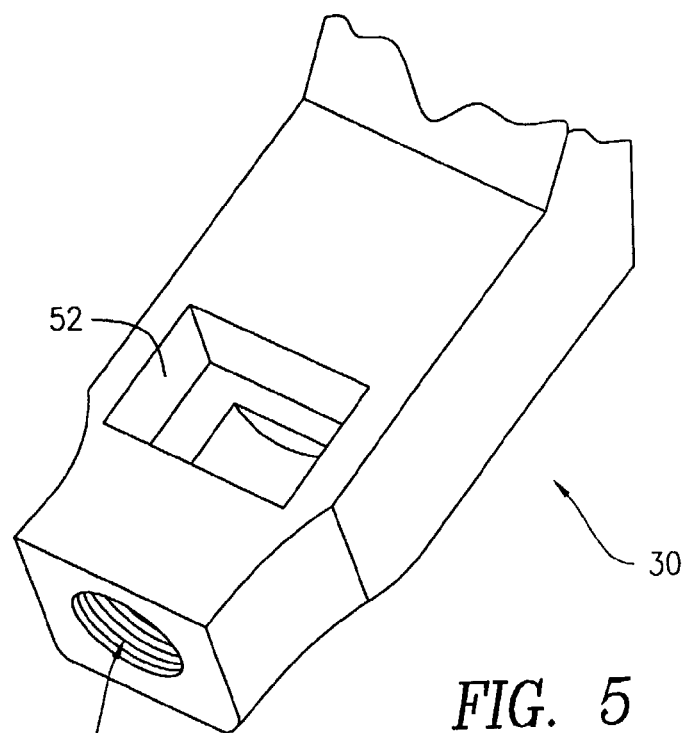
FIG. 5 is an enlarged view of a cutting jaw of the trimming device of FIG. 2 viewed from the perspective indicated by the arrow emanating from the letter "C" in FIG. 2 and with the cutter and cutter retention screw removed therefrom.

FIG. 5 shows cutting jaw 30 with cutter 28 and cutter retention screw 32 removed. A square aperture 52 receives base 54 (See FIG. 7) from which cutter 28 projects. A threaded hole 56 receives cutter retention screw 32 (FIG. 7) and communicates with aperture 52 such that the retention screw 32 can press against base 54, holding it in the cutting jaw 30. Aperture 52 and base 54 can have other mating shapes that allow keyed orientation and prevent rotation. Cutter 28 can therefore be replaced when it becomes dull or otherwise damaged. Cutter 28 may also be replaced with a cutter 28 of different cross-sectional profile. The cutter slot 42 and the edge 44 in holding jaw 26 may also be removable to match the cross-sectional profile of the cutter 28.

Figure 6:
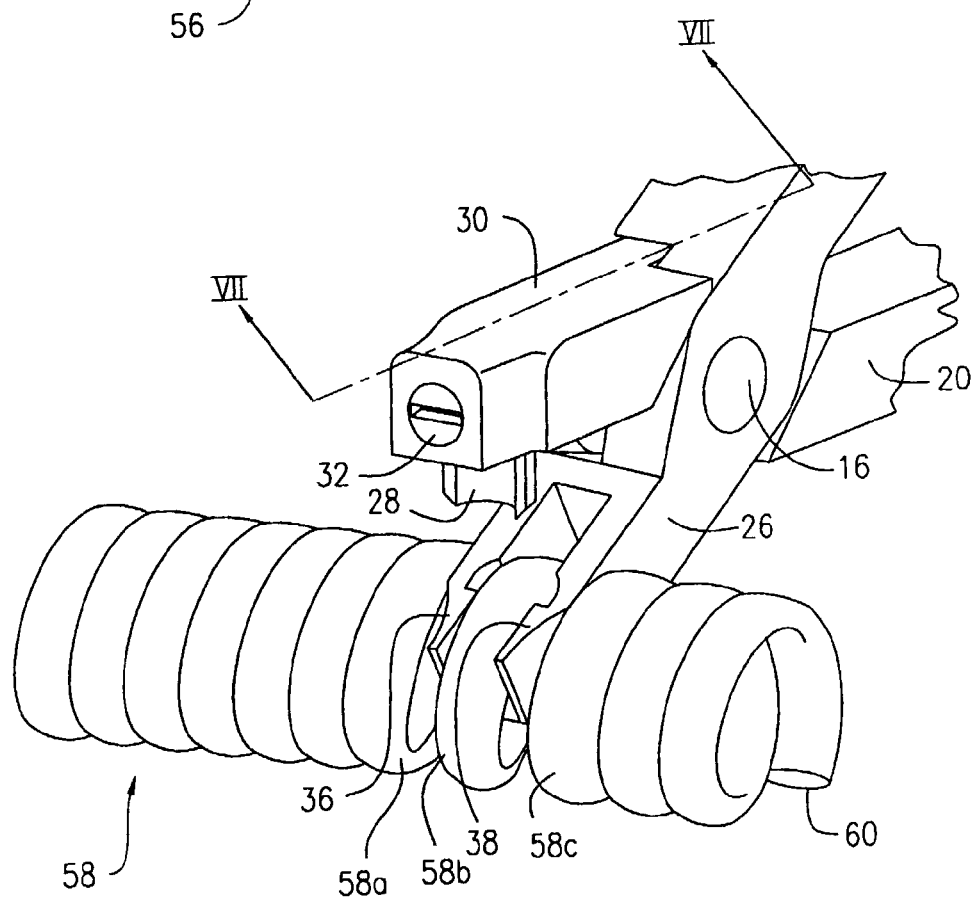
FIG. 6 is an enlarged view of the trimmer of FIG. 2, showing a coiled fiber loaded into the device.
Figure 7:
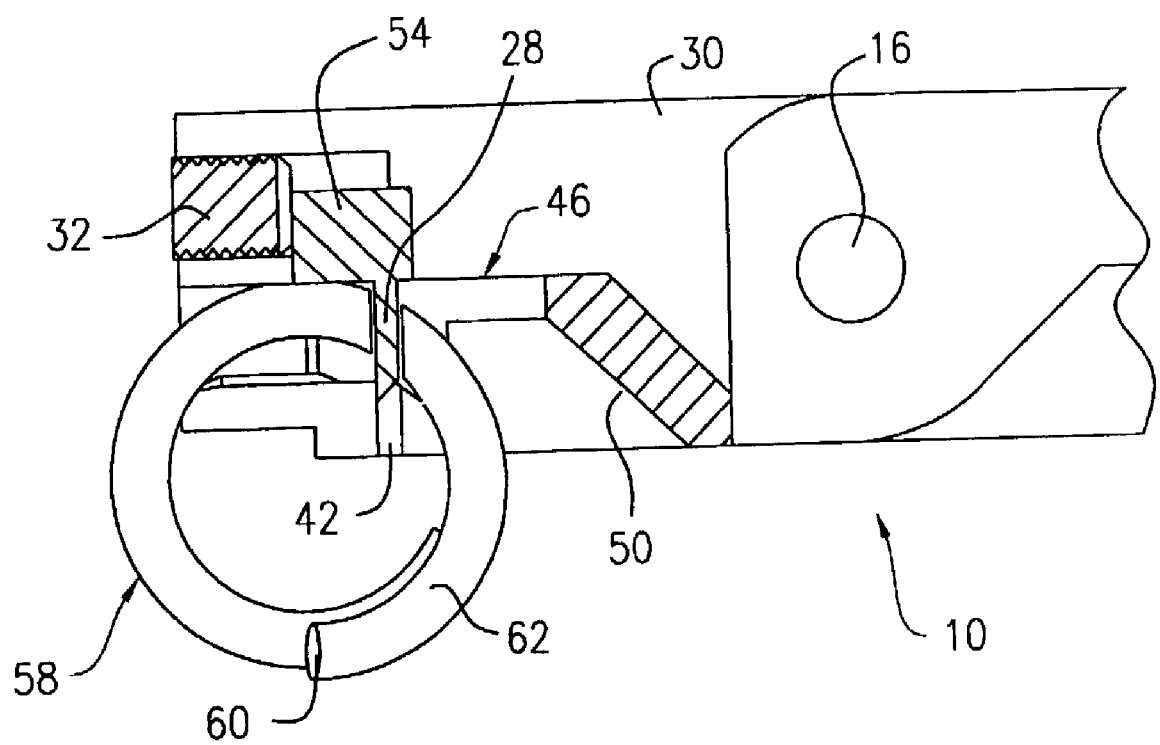
FIG. 7 is a cross-sectional view of the trimmer of FIG. 6 in a closed position having cut the fiber; taken along the cross-section line VII-VII and looking in the direction of the arrows.

In the embodiment shown in FIGS. 1, 2 and 6, cutter 28 has a semicircular cross-section, which produces a strand with a rounded cut end 64 (FIG. 8) as described below. A rounded cut end 64 is less prone to cut or pierce tissue into which it comes into contact. Referring to FIGS. 6 and 7, the trimmer 10 may be used to cut a coiled fiber or wire to a desired length leaving a rounded cut end 64 by the following method. Namely, by placing an end 60 of a coiled strand 58, such as a stent, between the side walls 36, 38 with the axis of the coiled strand 58 perpendicular to the guiding channel 34. The coiled strand 58 is then rotated about its axis until the end 60 exits the coil passageway 46. Rotation is continued, threading the coiled strand 58 through the holding jaw 26 until the strand 58 is properly positioned beneath the cutter 28, i.e., to provide the selected cut length. The cut is performed by applying compressive force to the arms 12, 14, causing the cutter 28 to be driven through the strand 58 and into the cutter slot 42.

FIG. 6 shows a coiled strand 58 loaded in holding jaw 26 of trimming device 10. End 60 of coiled strand 58 is threaded onto holding jaw 26 as described above, such that side walls 36, 38 are between adjacent individual coil turns 58a, 58b, 58c of the coiled strand 58. Arms 12, 14 are then squeezed together, closing cutting jaw 30 on holding jaw 26 and cutting coiled strand 58.

Figure 8:
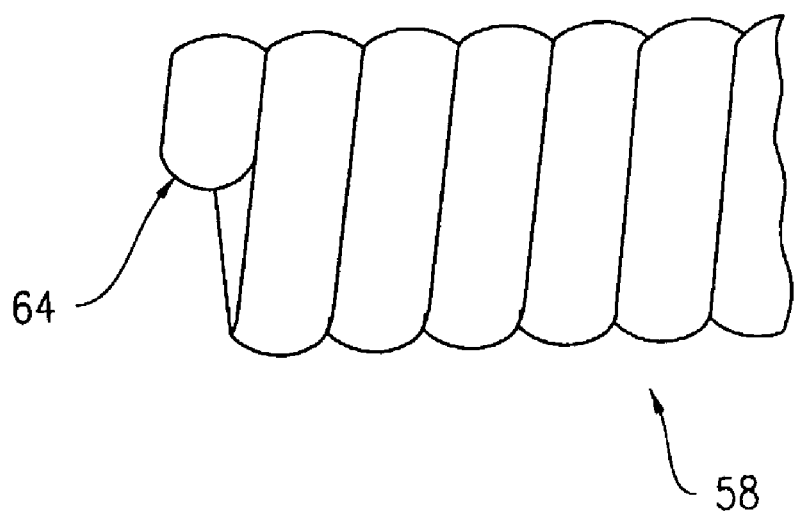
FIG. 8 is a side view of a coiled fiber with a rounded end produced by trimming the coiled fiber with a trimmer in accordance with the present invention.

FIG. 7 shows the trimmer 10 in the closed position with the cutter 28 fully through coiled strand 58. The cut portion 62 of coiled strand 58 is discharged from coil passage 46 of holding jaw 26. FIG. 8 shows coiled strand 58 with a rounded cut end 64, as would be produced by cutting the coiled strand 58 with a trimmer 10.

Trimmer 10 may be made of metals, such as carbon steel, stainless steel or titanium. If trimmer 10 is reusable, cutter 28 must have sufficient strength and hardness so as to make multiple cuts through the materials that comprise the coiled fiber or wire. If a disposable embodiment of trimmer 10 were desired, polymers may be incorporated for economical production.

The invention claimed is:

1. A cutting device for trimming a coiled strand, comprising:
   a pair of articulating arms pivotally connected at a pivot joint, each of said pair of articulating arms having a lever portion disposed proximal to said pivot joint and a jaw portion disposed distal to said pivot joint, said jaw portions being urged together when said lever portions are urged together, a first of said jaw portions being a holding jaw for holding the coiled strand and a second of said jaw portions being a cutting jaw for cutting the coiled strand, said holding jaw having an upper surface proximate to said cutting jaw, a lower surface distal to said cutting jaw, and a passageway extending through said holding jaw and through said upper surface and said lower surface through which the coiled strand may be threaded to hold the coiled strand for cutting the coiled strand at a selected location by said cutting jaw, said holding jaw having a guide channel defined by a bottom wall extending from a distal end of said holding jaw to said passageway and a first side wall extending substantially perpendicularly from said bottom wall, said first side wall positionable between adjacent turns of the coiled strand when said coiled strand is threaded through said passageway, the coiled strand retaining a coiled configuration along substantially the entire length thereof including the portion thereof which extends through the holding jaw.

2. The cutting device of claim 1, further comprising a second side wall extending from said bottom wall generally parallel to and spaced from said first side wall, the coiled strand passing between said first and second side walls when said coiled strand is threaded through said passageway.

3. The cutting device of claim 2, wherein said first and second side walls taper down in thickness in the direction extending from said pivot joint to a distal end of said holding jaw.

4. The cutting device of claim 3, wherein said bottom wall is radiused at a distal end thereof to more closely approximate an interior curvature of the coiled strand.

5. The cutting device of claim 4, where said bottom wall is radiused proximate to said passageway to more closely approximate an interior curvature of the coiled strand.

6. The cutting device of claim 5, wherein the coiled strand is held by said holding jaw in an orientation with an axial length of said coil disposed approximately perpendicularly to said articulating arms.

* * * * *